(12) United States Patent
Nakamura (10) Patent No.: US 7,942,378 B2
(45) Date of Patent: May 17, 2011

(54) TORQUE TRANSMITTING MECHANISM FOR MEDICAL STAND

(75) Inventor: Katsushige Nakamura, Mitaka (JP)

(73) Assignee: Mitaka Kohki Co., Ltd, Tokyo (JP)

( * ) Notice: Subject to any disclaimer, the term of this patent is extended or adjusted under 35 U.S.C. 154(b) by 620 days.

(21) Appl. No.: 11/867,297

(22) Filed: Oct. 4, 2007

(65) Prior Publication Data

US 2008/0083856 A1 Apr. 10, 2008

(30) Foreign Application Priority Data

Oct. 5, 2006 (JP) ................................. 2006-274182

(51) Int. Cl.
*F16M 13/00* (2006.01)
(52) U.S. Cl. ... 248/564; 248/569; 248/636; 248/123.11; 359/384
(58) Field of Classification Search ................... 248/564, 248/568, 569, 636, 123.11; 359/368, 382, 359/384; 267/262
See application file for complete search history.

(56) References Cited

U.S. PATENT DOCUMENTS

| | | | |
|---|---|---|---|
| 5,186,422 A * | 2/1993 | Nakamura | 248/123.2 |
| 5,528,417 A | 6/1996 | Nakamura | |
| 5,812,301 A * | 9/1998 | Nakamura | 359/384 |
| 6,105,909 A * | 8/2000 | Wirth et al. | 248/123.2 |
| 6,646,798 B2 * | 11/2003 | Schmidt et al. | 359/382 |
| 7,283,296 B2 * | 10/2007 | Nozawa et al. | 359/384 |
| 2004/0190131 A1 | 9/2004 | Brenner et al. | |
| 2005/0167550 A1 | 8/2005 | Poxleitner | |
| 2006/0108958 A1 | 5/2006 | Brenner et al. | |
| 2006/0291045 A1* | 12/2006 | Nakamura et al. | 359/384 |

FOREIGN PATENT DOCUMENTS

EP 0 628 290 A1 12/1994

OTHER PUBLICATIONS

European Search Report Dated Nov. 20, 2008.

* cited by examiner

*Primary Examiner* — Terrell McKinnon
*Assistant Examiner* — Bradley H Duckworth
(74) *Attorney, Agent, or Firm* — Edell, Shapiro & Finnan, LLC (57) ABSTRACT

The medical stands is used to support a medical tool and includes a first parallel linkage to maintain weight balance of the medical tool. The torque transmitting mechanism maintains an attitude of the medical tool and includes a second parallel linkage whose one end is fixed to a body of the medical stand, a connecting element, and a third parallel linkage connected through the connecting element to the second parallel linkage. Links that form the second parallel linkage are made of rigid material. A vibration suppressing mechanism is attached to a longitudinal link of the first parallel linkage and is always resiliently in contact with a longitudinal link of the second parallel linkage.

9 Claims, 8 Drawing Sheets

TORQUE TRANSMITTING MECHANISM FOR MEDICAL STAND

BACKGROUND OF THE INVENTION

1. Field of the Invention

The present invention relates to a medical stand capable of always balancing the weight of a load and maintaining an attitude of the load, and particularly, to a torque transmitting mechanism for maintaining an attitude of such a medical stand, capable of suppressing small vibrations occurring in the torque transmitting mechanism.

2. Description of the Related Art

A medical stand is an apparatus used to move a medical tool or a load to an optional position and keep the same at the position. A typical example of the medical stand is disclosed in Japanese Unexamined Patent Application Publication No. 6-197912. The medical stand disclosed in this publication is designed to support a medical tool such as a surgical microscope and has a mechanism for always balancing the weight of the medical tool wherever the medical tool is moved and a mechanism for maintaining an attitude or orientation of the medical tool with respect to a reference plane wherever the medical tool is moved to.

Figure 1:
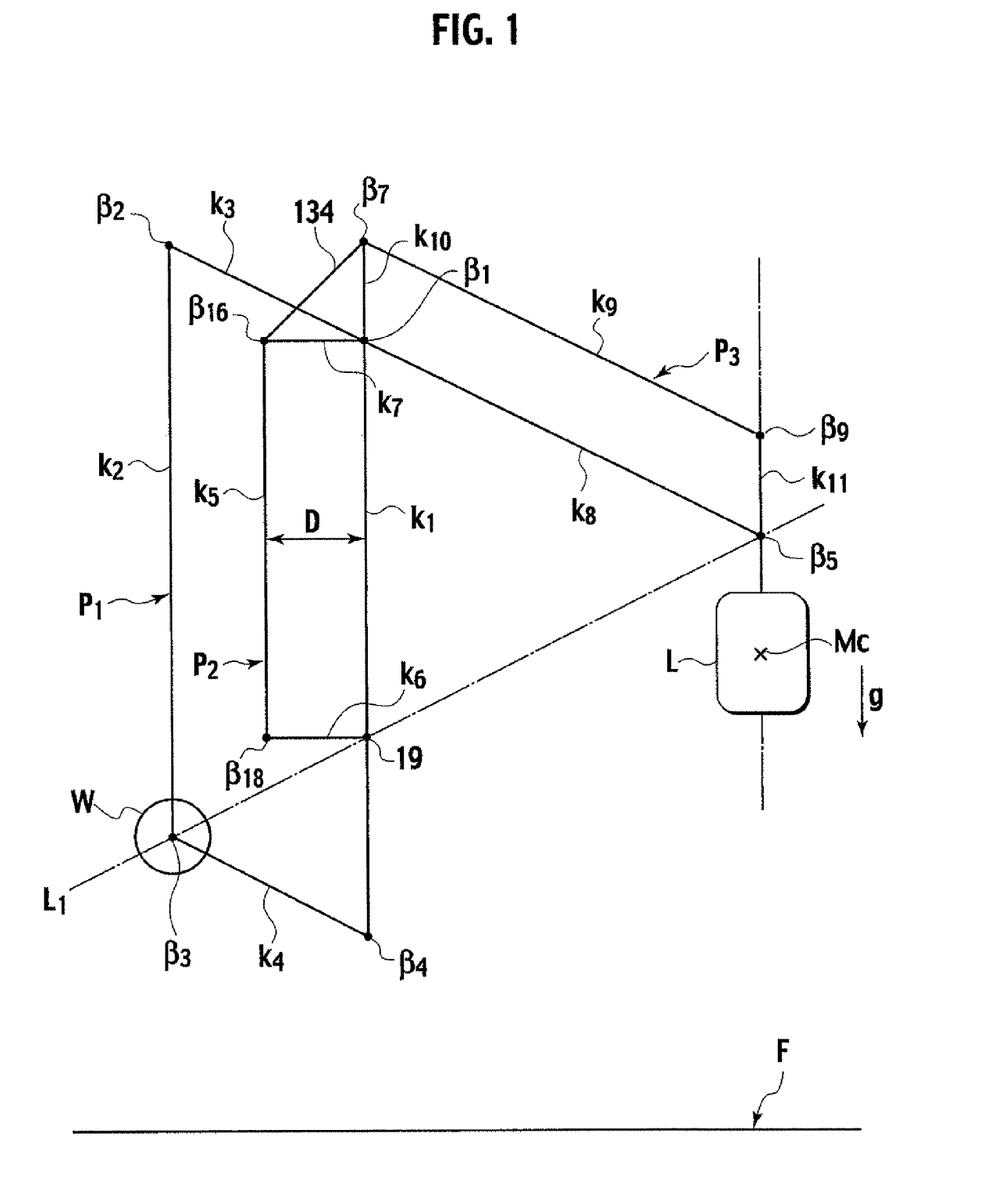
FIG. 1 is a schematic view showing parallel linkages of a medical stand according to a related art.

FIG. 1 is a model view showing parallel linkages employed by the medical stand according to the above-mentioned related art. Among the parallel linkages, a first parallel linkage P1 includes two longitudinal links k1 and k2 and two lateral links k3 and k4. At an intermediate point 19 of the link k1, the first parallel linkage P1 is supported by a body of the medical stand (not shown) that is positionally fixed to a reference plane F such as a floor surface. The links k2 and k4 are rotatably connected to each other with a shaft as a joint β3 that supports a counterweight W. The links k3 and k1 are rotatably connected to each other with a joint β1. The link k3 is integral with a lateral link k8 that is rotatably connected to a joint β5 for supporting a load L. The load L is a medical tool in the embodiment. According to the principle of a parallel linkage, the counterweight W, the intermediate joint 19, and the load supporting joint β5 are always on a virtual straight line L1. Wherever the load L is positioned, the first parallel linkage P1 balances the weight of the load L with the counterweight W around the joint 19 serving as a fulcrum.

A second parallel linkage P2 includes the longitudinal link k1 common to the first and second parallel linkages P1 and P2, a longitudinal link k5, and two lateral links k6 and k7. The link k6 is fixed relative to the medical stand body (not shown). A third parallel linkage P3 includes two longitudinal links k10 and k11 and two lateral links k8 and k9. The link k8 is integral with the link k3 of the first linkage P1. The joint β1 is a common joint to the first, second, and third parallel linkages P1, P2, and P3. The link k10 of the third parallel linkage P3 is coupled with the link k7 of the second parallel linkage P2 through a crank or a connecting element 134. The orientation of a primary axis of the front link k11 with respect to the lateral link k6 is thus always fixed through the third parallel linkage P3, crank 134, and second parallel linkage P2. As a result, the front link k11 is always oriented plumb (gravity direction g) wherever the load L is moved to. The center of gravity Mc of the load L is right below the joint β5 at a lower end of the front link k11. The second parallel linkage P2, crank 134, and third parallel linkage P3 form a torque transmitting mechanism acting between the link k6 fixed to the medical stand body and the link k11 supporting the load L. The joints 19, β1, and β5 are equivalent to one another in terms of torque transmission. The direction of plumb mentioned above is in parallel with the direction of gravitational force and includes, for example, centrifugal force.

In this way, the medical stand shown in FIG. 1 employs very simple mechanisms to maintain the weight balance of the load L such as a surgical microscope wherever the load L is moved and also keep a posture or tilt of the load L.

When a surgeon conducts a microscopic operation on a patient by observing an enlarged image of an affected part provided by a surgical microscope supported on the medical stand, the medical stand maintains the weight balance of the surgical microscope that usually weighs over 20 kg, allows the surgeon to easily move the surgical microscope to a required position and stop the same at the position, and provides the surgeon with stabilized images of the affected part by maintaining an attitude (tilt) of the surgical microscope during the movement of the surgical microscope.

SUMMARY OF THE INVENTION

The medical stand shown in FIG. 1 is useful for a neurosurgery operation that uses a high-power surgical microscope. When using such a high-power surgical microscope, images from the microscope should not be affected by small vibrations that may occur in the medical stand. In the medical stand of FIG. 1, the primary axis of the front link k11 is substantially oriented to a vertical direction and the center of gravity Mc of the surgical microscope (load) L is just below the joint β5. Due to this configuration, an average bias of torque transmitted from the front link k11 to the second and third parallel linkages P2 and P3 is substantially zero to hardly cause vibration. The configuration of FIG. 1, therefore, is essential for a high-power surgical microscope.

Figure 2:
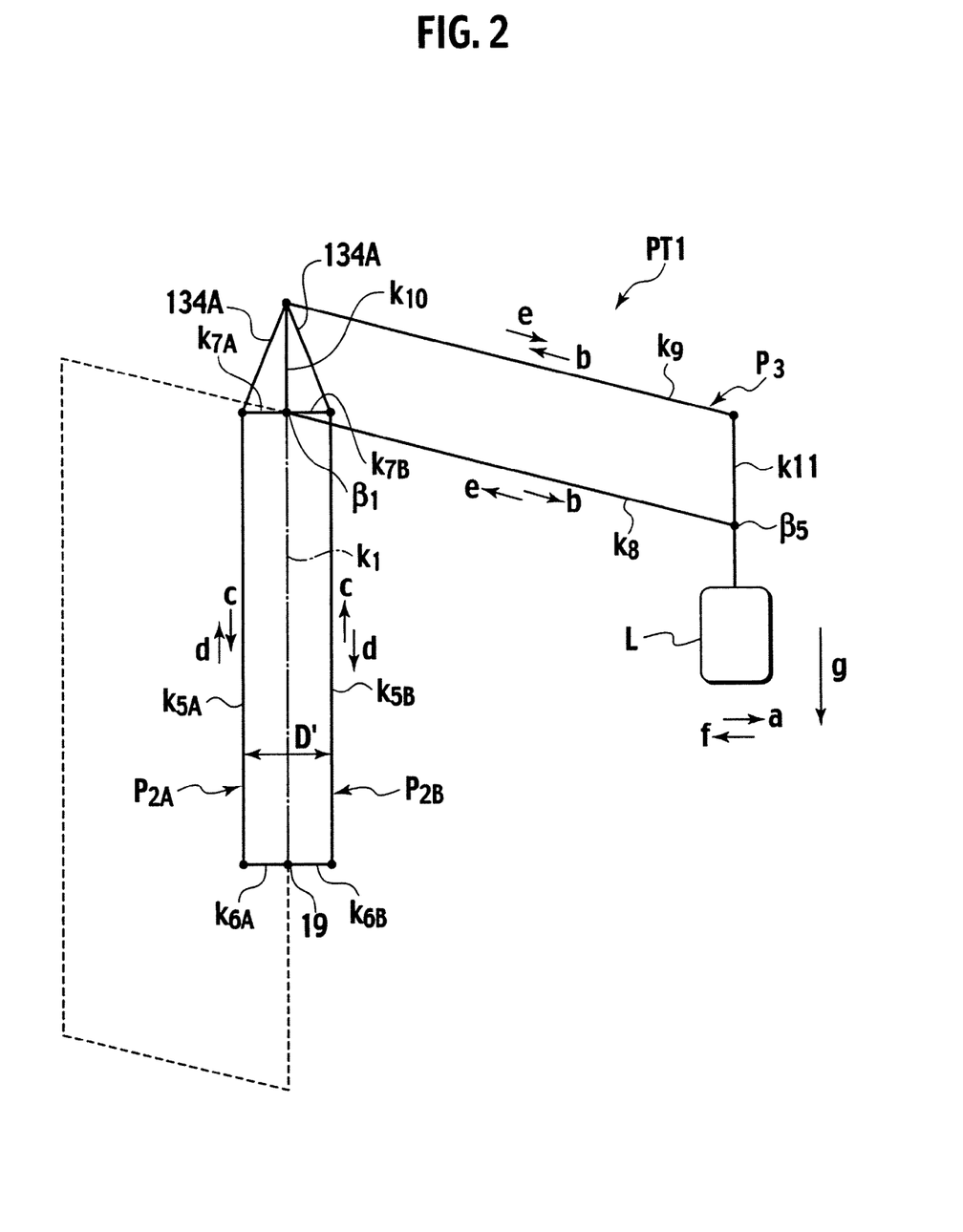
FIG. 2 is a schematic view showing a torque transmitting mechanism for a medical stand, according to a related art.

There is a need of reducing the width D of the second parallel linkage P2 to make the medical stand compact and improve the operability thereof. FIG. 2 shows a medical stand that replaces the second parallel linkage P2 of FIG. 1 with two narrow sub-linkages, to realize a narrow total width D'. In FIG. 2, the first parallel sub-linkage P2A includes two lateral sub-links k7A and k6A and two longitudinal sub-links k5A and k1, and the second parallel sub-linkage P2B includes two lateral sub-links k7B and k6B and two longitudinal sub-links k5B and k1. The sub-linkages P2A and P2B are equivalent to the second parallel linkage P2 of FIG. 1. A joint β1 is common to the two sub-linkages P2A and P2B and a third parallel linkage P3. A longitudinal link k10 of the third parallel linkage P3 is linked with the sub-linkages P2A and P2B through a crank 134A as connecting element.

<Small Vibration of Load>

In FIG. 2, a lower end of a front link k11 is attached to a load L such as a surgical microscope. The front link k11 is substantially oriented to a vertical direction. When an operation "a" is conducted on the microscope L, small torque is produced around a joint β5 at the lower end of the front link k11. The small torque causes a small deformation in terms of a small tilt "b" of the third parallel linkage P3. The small tilt "b" causes a small deformation "c" of the second parallel linkage P2 through the crank 134A, to transmit the small torque to the lateral link k6 (k6A, k6B). The link k6 (k6A, k6B) is fixed to the medical stand body, and therefore, causes a reaction to reflect the small torque. The reflected torque causes a small deformation as depicted by "d" of the second parallel linkage P2 and a small deformation as depicted by "e" of the third parallel linkage P3, to slightly displace the front link k11. As a result, the load L moves in a direction as depicted by "f".

The second parallel linkage P2 (P2A, P2B), crank (connecting element) 134A, and third parallel linkage P3 form a torque transmitting mechanism PT1 between the lateral link k6 (k6A, k6B) fixed to the medical stand body and the front link k11 supporting the load L. If anywhere in the torque transmitting mechanism PT1 produces small torque around the joints 19, β1, and β5, a force corresponding to the small torque will be reflected between the load L and the link k6 (k6A, k6B). This will result in producing small vibrations of the load L and amplifying such small vibrations. The small vibrations of the load L raise a severe problem if the load L is a high-power surgical microscope and is used for suturing capillaries. If the width D' of the second parallel linkage P2 is sufficiently large, the reflection of small torque will properly attenuate. As the width D' narrows, a working radius becomes smaller to enlarge a force or a change of force applied to the links k1 and k5 (k5A, k5B). This results in increasing the reflection of force and the vibration of images provided by the surgical microscope. This tendency becomes conspicuous when each link of the second parallel linkage P2 is made of a bar of high rigidity to realize a high-speed transmission of force.

A related art disclosed in U.S. Patent Application No. 2005/0167550A1 discloses a flexible force transmitting element such as a belt that can be tensioned and is usable as the longitudinal link k5 (k5A, k5B) of the second parallel linkage P2 (P2A, P2B) of FIG. 2. The belt is stretched around a first pulley corresponding to the lateral link k7 (k7A, k7B) of the second parallel linkage P2 and a second pulley corresponding to the lateral link k6 (k6A, k6B) of the second parallel linkage P2. The first pulley is rotatably supported at the joint β1 and is connected as the crank 134A to the third parallel linkage P3. The second pulley is fixed to the body of a medical stand. This medical stand may provide a function similar to that provided by the medical stand disclosed in the above-mentioned Japanese Unexamined Patent Application Publication No. 6-197912. The force transmitting flexible element serving as the longitudinal link k5 (k5A, k5B) may prevent transmission of small torque. Compared with a bar of high rigidity, the flexible material such as a belt or rope used for the force transmitting flexible element has a smaller force transmitting ability. The belt is substantially unable to resist against a compressive force acting in a length direction, and therefore, one of the belt segments between the two pulleys alternately works for the second parallel linkage P2. As a result, an effective width of the second parallel linkage P2 is practically a distance of D'/2 between the link k1 and the sub-link k5A (or k5B). If a small torque variation occurs to shift the front link k11 and load L from a balanced position, the sub-linkages P2A and P2B will alternately transmit a tensile force. Then, the front link k11 will not be kept in plumb and a position of the load L will be unstable according to circumstances. In addition, the flexible material has a slow force transmitting speed, and therefore, small vibrations will not be suppressed in a case where the width D' of the second parallel linkage P2 is narrow. Depending on specific vibration components in the torque transmitting mechanism PT1, the torque transmitting mechanism PT1 as a whole will cause small vibrations and enhance them. Small torque produced by the second parallel linkage P2 will be transmitted through the connecting element (134A) to the third parallel linkage P3 to slightly vibrate the surgical microscope to prevent an operator from observing stable images from the microscope.

There is a need, therefore, for a torque transmitting mechanism for a medical stand, capable of reducing the width of a second parallel linkage (P2) without causing small vibrations.

In consideration of the above-mentioned problems and need, an object of the present invention is to provide a torque transmitting mechanism for a medical stand, capable of maintaining the weight balance and attitude of a medical tool or a load supported with the medical stand, reducing the width of a second parallel linkage (P2), and causing no vibration or amplification of vibration of the load.

According to an aspect of the present invention, provided is a torque transmitting mechanism for a medical stand that includes a first parallel linkage as a first quadrilateral linkage linked through a first joint (first articulation), a second joint (second articulation), a third joint (third articulation) opposing the first joint, and a fourth joint (fourth articulation) opposing the second joint, the first and fourth joints being connected to each other with a first longitudinal link, the second and third joints being connected to each other with a second longitudinal link extending in parallel with the first longitudinal link, the first and second joints being connected to each other with a first lateral link, the third and fourth joints being connected to each other with a second lateral link extending in parallel with the first lateral link, the first longitudinal link having, at an intermediate position thereof, a fifth joint (fifth articulation) positionally fixed to a stand body of the medical stand, the first lateral link being coupled with an eighth joint (eighth articulation), the third joint supporting a counter weight. The torque transmitting mechanism also includes a second parallel linkage as a second quadrilateral linkage linked through the first joint, the fifth joint, a sixth joint (sixth articulation) opposing the first joint and positionally fixed to the stand body, and a seventh joint (seventh articulation) opposing the fifth joint, the sixth and seventh joints being connected to each other with a third longitudinal link extending in parallel with the first longitudinal link, the first and seventh joints being connected to each other with a third lateral link, the fifth and sixth joints being connected to each other with a fourth lateral link extending in parallel with the third lateral link, the first and third longitudinal links being made of rigid material; a third parallel linkage as a third quadrilateral linkage linked through the first joint, the eighth joint, a ninth joint (ninth articulation) opposing the first joint, and a tenth joint (tenth articulation) opposing the eighth joint, the first and eighth joints being connected to each other with a fifth lateral link, the ninth and tenth joints being connected to each other with a sixth lateral link extending in parallel with the fifth lateral link, the first and tenth joints being connected to each other with a fifth longitudinal link, the eighth and ninth joints being connected to each other with a sixth longitudinal link extending in parallel with the fifth longitudinal link, the third lateral link and fifth longitudinal link being coupled with a connecting element, the sixth longitudinal link being always in parallel with a vertical direction, the eighth joint supporting a medical tool just below the same; and a vibration suppressing mechanism positionally fixed to the first longitudinal link and configured to produce contact resistance to suppress vibration of the third longitudinal link that defines a tilt of the second quadrilateral linkage.

DESCRIPTION OF THE PREFERRED EMBODIMENT

A medical stand and a torque transmitting mechanism according to an embodiment of the present invention will be explained with reference to FIG. 3. The medical stand according to the present embodiment includes linkages similar to those of FIGS. 1 and 2. Namely, the medical stand according to the present embodiment includes a first parallel linkage P1, second parallel linkage P2, and third parallel linkage P3. The first parallel linkage P1 includes a link case 121, a longitudinal link 22 (β2-β3), and two lateral links 23 (β2-β1) and 24 (β3-β4). The link case 121 is equivalent to the longitudinal link kl (β1-β4) shown in FIGS. 1 and 2, is made of rigid material, and has a hollow structure accommodating and protecting the second parallel linkage P2. The link case 121 serving as a longitudinal link has an intermediate point that is supported with a joint 19 (fifth joint) fixed relative to a stand body 18 of the medical stand. The stand body 18 is fixed relative to a reference surface F such as a floor surface. The longitudinal link 22 and lateral link 24 are connected to each other through a joint P3 (third joint). The joint β3 supports counterweights W1 and W2 through the longitudinal link 22 and lateral link 24. The lateral link 23 and link case 121 are connected to each other through a joint β1 (first joint). The lateral link 23 extends to a lateral link 26 that is coupled with a support joint β5 (eighth joint). The joint β5 supports, just below the same, a load L such as a medical tool that may be a surgical microscope. Wherever the load L is, the weight of the load L balances with the counterweights W1 and W2 with respect to the joint 19 due to the first parallel linkage P1. The stand body 18 includes a base 16 and a frame. The base 16 has locking casters 17 and a vertical shaft around which the frame 18 is turnable through an electromagnetic clutch C1.

<Torque Transmitting Mechanism>

An attitude or a tilt of the load L is maintained by a torque transmitting mechanism having the second parallel linkage P2, a connecting element 34, and the third parallel linkage P3.

Figure 3:
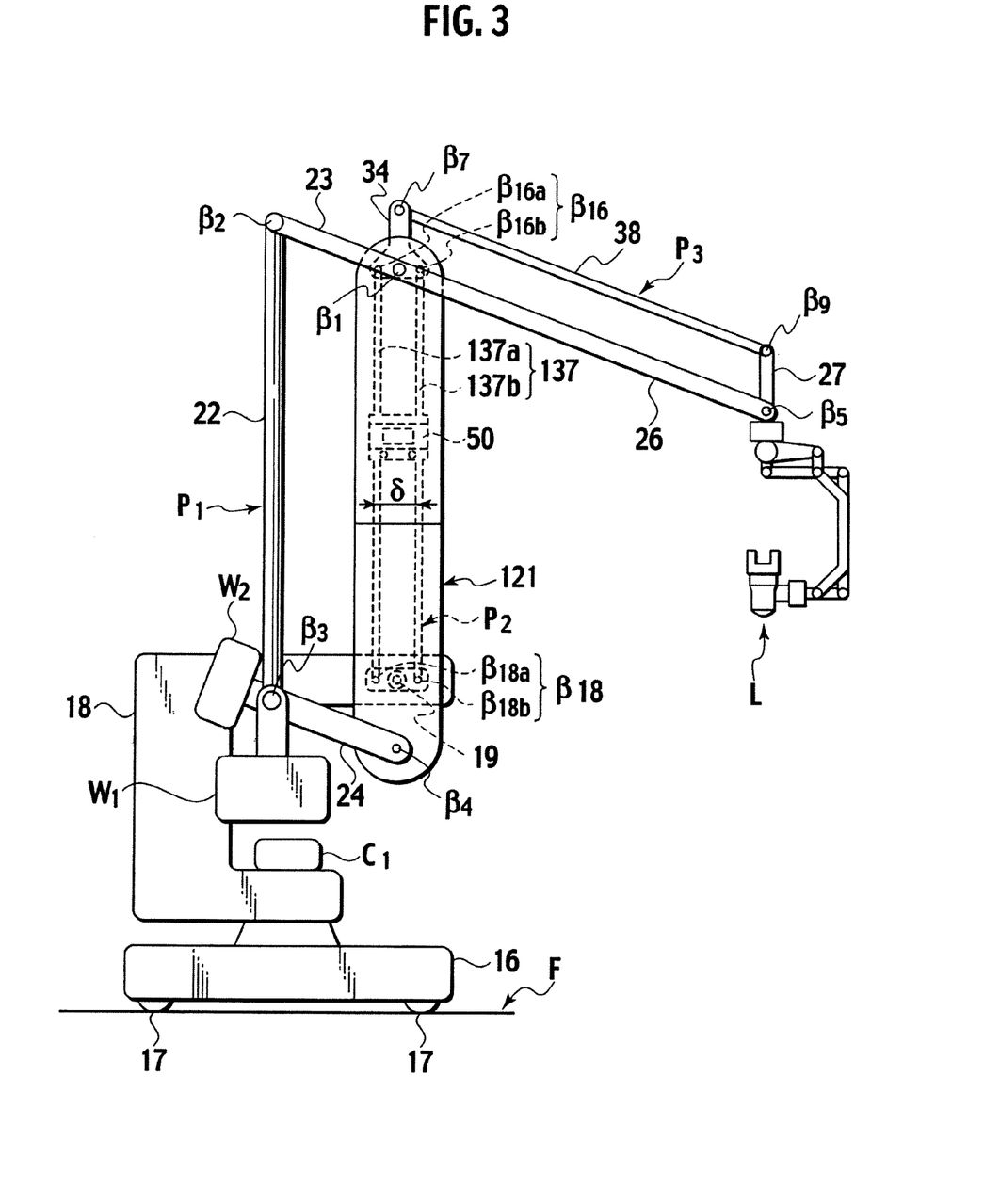
FIG. 3 is a view showing a medical stand and a torque transmitting mechanism according to an embodiment of the present invention.

In FIG. 3, the second parallel linkage P2 has two narrow parallel sub-linkages similar to the sub-linkages P2A and P2B of FIG. 2 and has a total width of δ. More precisely, the second parallel linkage P2 includes the link case 121 serving as a longitudinal link (common to the first parallel linkage P1) kl and a longitudinal link shaft 137 (137*a*, 137*b*) made of rigid material. A lower end of the link shaft 137 is connected to the stand body 18 through a joint β18 (β18*a*, β18*b*). An upper end of the link shaft 137 is connected to the connecting element (crank) 34 through a joint β16 (β16*a*, β16*b*). The crank 34 is supported with the joint β1. That is, the crank 34 connects the second parallel linkage P2 on the link k7 (β1-β16) and the third parallel linkage P3 on the link k10 (β1-β7) in terms of a predetermined angle about the joint β1, so that the link k7 and the link k10 are fixed relative to each other.

A plate spring 51 serving as a vibration suppressing mechanism 50 is positionally fixed to the link case 121 as the link k1, so that the plate spring 51 is always resiliently in contact with the link shaft 137. The third parallel linkage P3 includes the crank 34 (β1-β7), a front longitudinal link 27, and lateral links 26 and 38. These links are connected together through the joints β1, β5, β7, and β9. The torque transmitting mechanism including the second and third parallel linkages P2 and P3 fixes a tilt of the front link 27 relative to a virtual link β18-19 of the stand body 18, so that a primary axis of the front link 27 is always oriented to a predetermined direction such as plumb. Using the link shaft 137 that is rigid and hard as a longitudinal link is effective to resist against compressive/tensile force in the primary axis direction, avoid deformation, and transmit sufficient torque.

<Parallel Linkages>

According to the present embodiment, each parallel linkage is made of hard link bars. A parallel linkage according to the present invention is defined as a quadrilateral linkage element linked through a first articulation, a second articulation, a third articulation opposing the first articulation, and a fourth articulation opposing the second articulation, wherein the first and fourth articulations are connected to each other with a first longitudinal side element, the second and third articulations are connected to each other with a second longitudinal side element extending in parallel with the first longitudinal side element, the first and second articulations are connected to each other with a first lateral side element, the third and fourth articulations are connected to each other with a second lateral side element extending in parallel with the first lateral side element, and the side elements are movable to define a tilt of the quadrilateral linkage element.

Each of the side elements of the quadrilateral linkage element is typically a link bar and each of the articulations includes typically a rotary shaft as a joint. Such a configuration, however, does not limit the present invention. For example, a parallel linkage according to an embodiment of the present invention may have two sprockets, part or the whole of an endless chain serving as a force transmitting element that can be tensioned, and a hard link bar supporting the centers of the two sprockets and applying a tensile force to the chain. In this linkage, each end of an acting area where the sprocket and chain interact with each other is a virtual articulation or disjunction point and the sprocket-chain structure includes four such articulations. The four disjunction points define two quasi-parallel sub-linkages with the hard link bar serving as a common link, like the parallel sub-linkages P2A and P2B of FIG. 2. If one of the sprockets is rotationally fixed and the parallel linkage is virtually tilted by a small angle, the other sprocket will slightly tilt and the joints thereof will slightly move along the sprocket. This is equivalent to a phenomenon that occurs in a parallel linkage made of link bars. The phenomenon also occurs when the parallel linkage is continuously tilted.

If the chain mechanism mentioned above is applied to the third parallel linkage P3 connected to the connecting element 34, one of the sprockets should be fixed to or integral with the connecting element 34.

The chain, like a belt, is substantially unable to resist against a compressive force, and therefore, needs a tensile force when used as a member of a parallel linkage. For this, the rigid link bar mentioned above is used as a link of the parallel linkage, to support the two sprockets and apply a tensile force to the chain. The two quasi-parallel sub-linkages employing a chain complementarily act as a single parallel linkage. In this case, an effective width of the parallel linkage serving as a torque transmitting element is about half the physical width of the parallel linkage (i.e. half the diameter of the sprocket).

<Vibration Suppressing Mechanism>

In FIG. 3, the second parallel linkage P2 with one side element thereof fixed relative to the stand body 18 and the third parallel linkage P3 connected through the connecting element 34 to the second parallel linkage P2 serve as a torque transmitting mechanism between the front link 27 and the stand body 18. If the front link 27 causes a small attitude change to produce torque, the torque will be transmitted through the torque transmitting mechanism to a virtual link (19-β18) fixed to the stand body 18. Then, the virtual link produces a reactive force, which is transmitted through the torque transmitting mechanism to the front link 27 to correct the attitude change and maintain the attitude of the front link 27. If the second parallel linkage P2 is made of only hard and rigid links, the second parallel linkage P2 can secure a force transmitting ability and a high transmission speed, can be resistive against compressive force (pressing force) and stretching force (tensile force), and can prevent meaningful deformation, thereby surely maintain an attitude of the front link 27. The second parallel linkage P2 has a physical width δ that is the width of the torque transmitting element realized by the second parallel linkage P2. Reducing the linkage width δ results in decreasing a working radius and increasing a force to be transmitted, which is preferable. However, reducing the linkage width δ enhances small vibrations around the front link 27 due to reflection of force. To prevent this, the present invention arranges the vibration suppressing mechanism 50 between the joints β1 and 19 of the link case 121, wherein the link case 121 is rigid and serves as the common longitudinal link k1 of the second parallel linkage P2 and first parallel linkage P1. Part of the vibration suppressing mechanism 50 is always resiliently in contact with a smooth side face of the rigid longitudinal link shaft 137 (137a, 137b).

Figure 4:
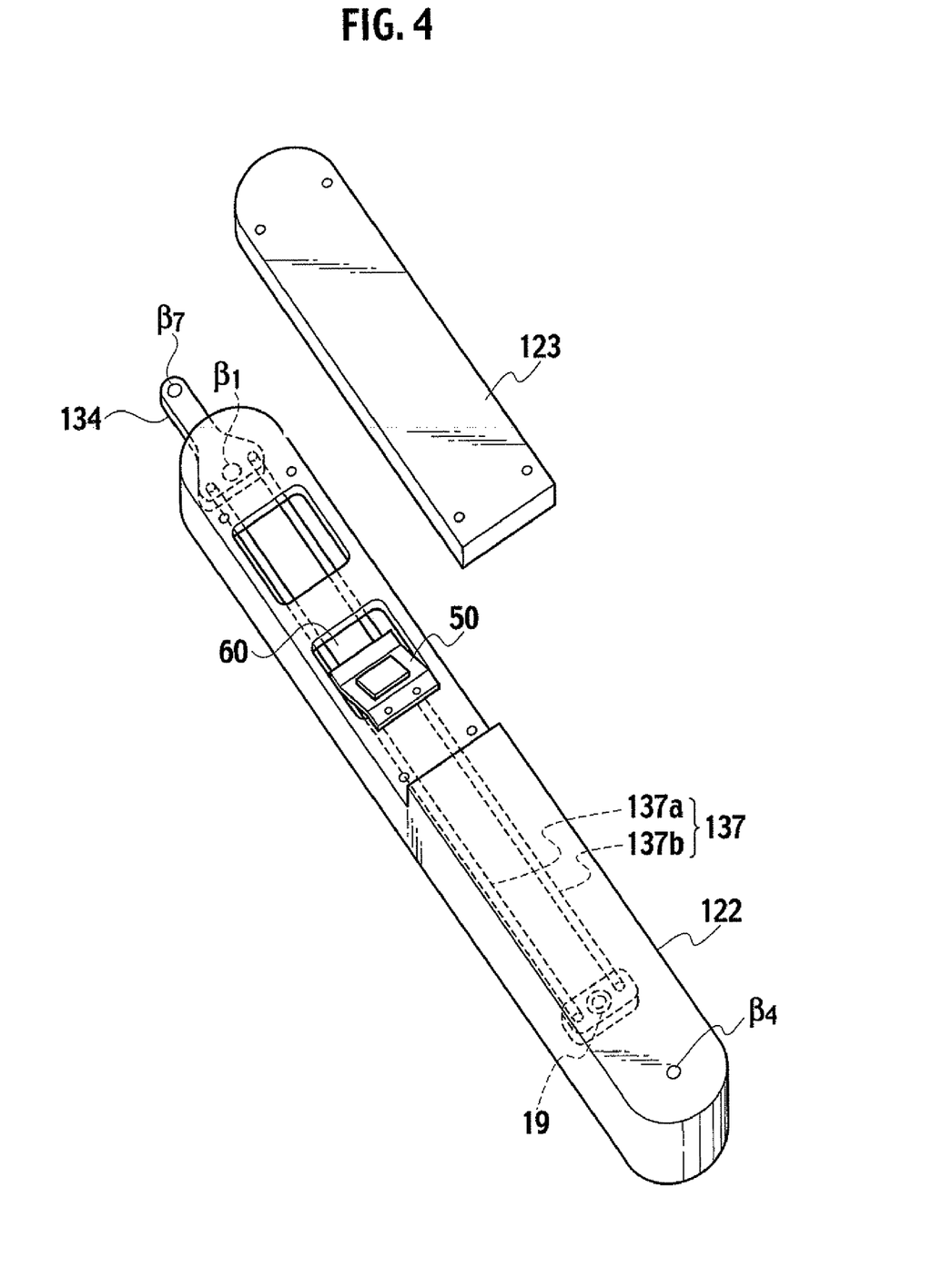
FIG. 4 is a perspective view showing a second parallel linkage in the torque transmitting mechanism of FIG. 3.
Figure 5:
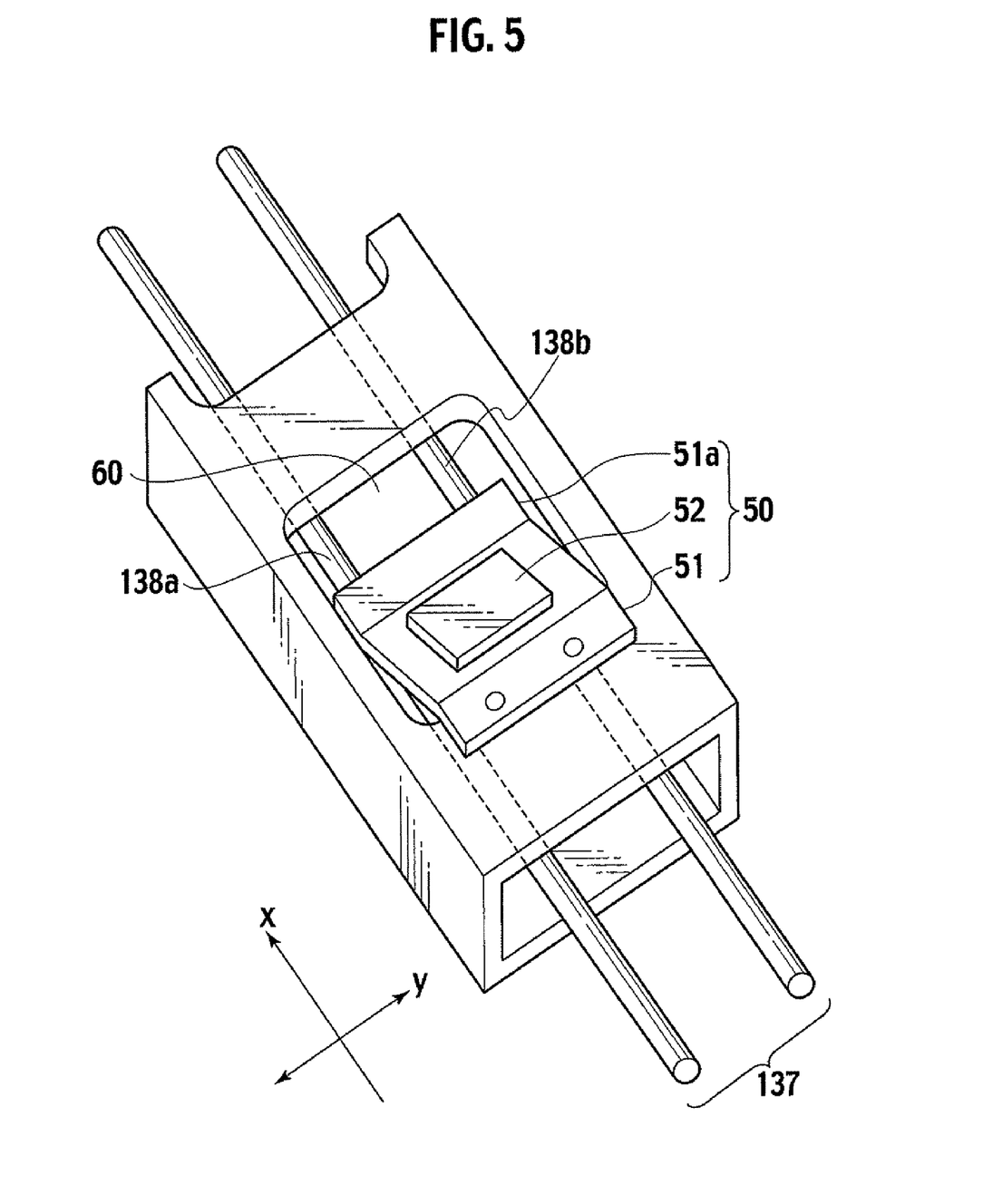
FIG. 5 is a perspective view showing a vibration suppressing mechanism provided for the second parallel linkage of FIG. 4.
Figure 6:
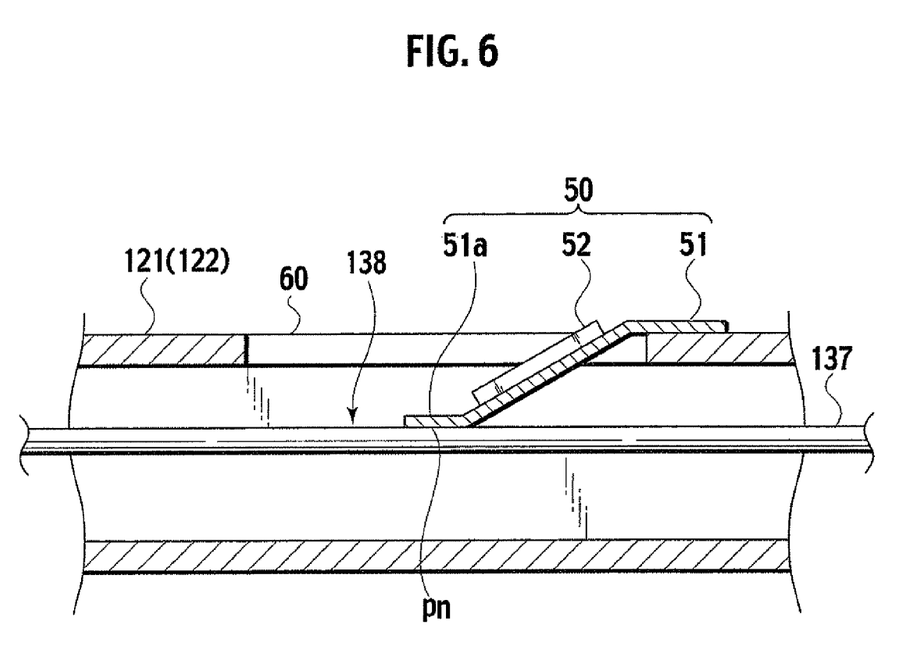
FIG. 6 is a sectional view showing the vibration suppressing mechanism of FIG. 5.

FIGS. 4 to 6 show the details of the vibration suppressing mechanism 50. The vibration suppressing mechanism 50 includes the plate spring 51 whose proximal end portion is fixed to a body 122 of the link case 121. A distal end 51a of the plate spring 51 passes through an opening 60 formed in the body 122 and is always resiliently in contact with the side face 138 (138a, 138b) of the link shaft 137 (137a, 137b). The distal portion of the plate spring 51 mainly provides resiliency and the proximal end 51a thereof is always in linear or planar contact with the side face 138 of the link shaft 137 to bias the side face 138.

The longitudinal link shaft 137 and the opposing longitudinal link case 121 move to define a tilt of the second parallel linkage P2. The vibration suppressing mechanism 50 is fixed to the link case 121 and is configured to make parallel linear or planar contact with a virtual line or plane along which the link shaft 137 moves when the second parallel linkage P2 tilts. Contact resistance between the vibration suppressing mechanism 50 and the link shaft 137 suppresses small vibrations of the second parallel linkage P2 having a large force transmission ability and a high transmission speed. Furthermore, the vibration suppressing mechanism 50 never brakes nor bothers a tilt of the second parallel linkage P2. For this, it is preferable that the distal end 51a of the vibration suppressing mechanism 50 has a line or plane that is parallel to the above-mentioned virtual plane.

The vibration suppressing mechanism 50 always biases the link shaft 137 to suppress small vibrations without regard to whether the second parallel linkage P2 is stationary or is moving to change its shape. The vibration suppressing mechanism 50 interacts with the link shaft 137 by sliding along the same, and therefore, produces no significant frictional resistance that may prevent the deformation of the second parallel linkage P2. The contact resistance (slide resistance) of the vibration suppressing mechanism 50, however, surely suppresses small vibrations. The small vibrations, if not suppressed, are repeatedly reflected between the ends of the torque transmitting mechanism and are enhanced by slight plays of the joints of the parallel linkages and slight deformations of the links of the parallel linkages, to badly affect observation of images from the high-power microscope L supported with the medical stand. As soon as vibrations occur, the vibration suppressing mechanism 50 suppresses the initial vibrations or growth of the vibrations by producing contact resistance that is small but enough to suppress slight displacements or vibrations.

The vibration suppressing mechanism 50 is not an active one that detects a slight displacement or vibration and feedback-controls an actuator connected to links, and therefore, is very simple, stable, and safe.

According to the embodiment, a primary axis of the link shaft 137 is in parallel with x-axis fixed to the link case 121. The link shaft 137 having link shafts 137a and 137b those are made of rigid material and are juxtaposed along y-axis direction that is orthogonal to the x-axis. That is, the link shafts 137a and 137b are movable in an x-y plane. The x-y plane is a virtual plane orthogonal to axes of the joints 19 and β1.

In FIGS. 5 and 6, the distal end 51a of the plate spring 51 has a surface pn that is parallel to a virtual plane defined by the relative movement of the link shafts 137 thereto and is in linear or planar contact with the side face 138 of the link shaft 137. Even if the second parallel linkage P2 tilts and deforms, a contact interaction between the distal end 51a of the plate spring 51 and the side face 138 of the link shaft 137 is always maintained. According to the embodiment, the link shaft 137 consists of the two link shafts 137a and 137b. If the second parallel linkage P2 tilts, the two link shafts 137a and 137b move in the same virtual plane, and therefore, are always in contact with and interact with the front end 51a of the plate spring 51 to produce contact resistance. A width δs (FIG. 9) of the distal end 51a of the plate spring 51 is determined so that the distal end 51a is always in contact with the link shafts 137a and 137b within the range of deformation of the second parallel linkage P2.

Figure 7:
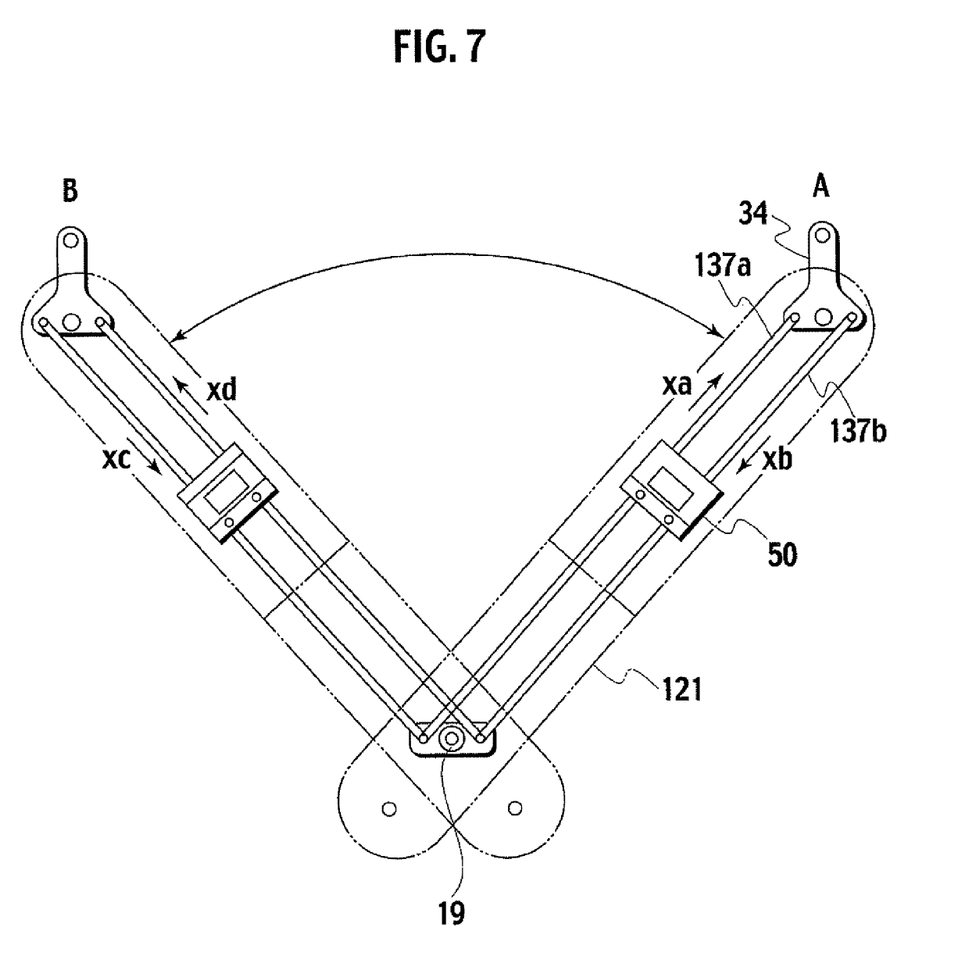
FIG. 7 is a view showing operation of the vibration suppressing mechanism as the second parallel linkage is tilted.
Figure 8:
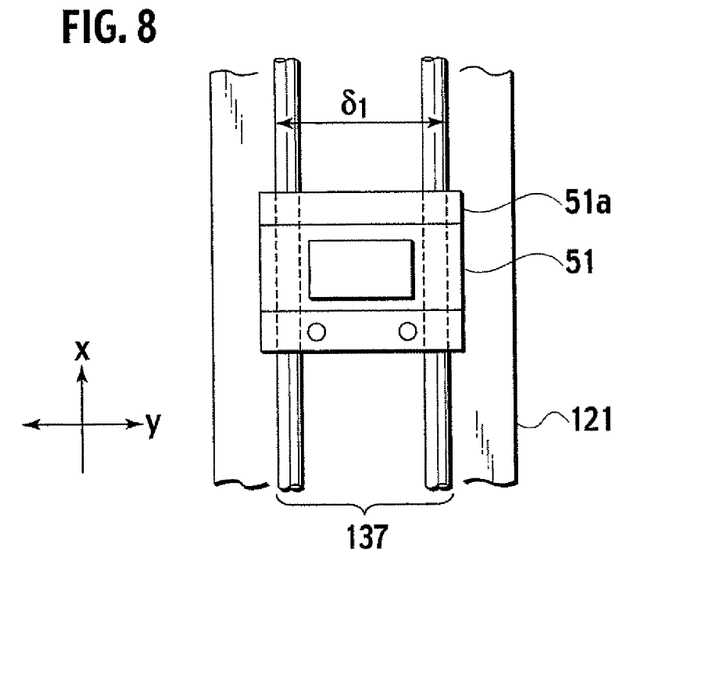
FIG. 8 is a view showing a state of the vibration suppressing mechanism with the second parallel linkage widened due to a tilt.
Figure 9:
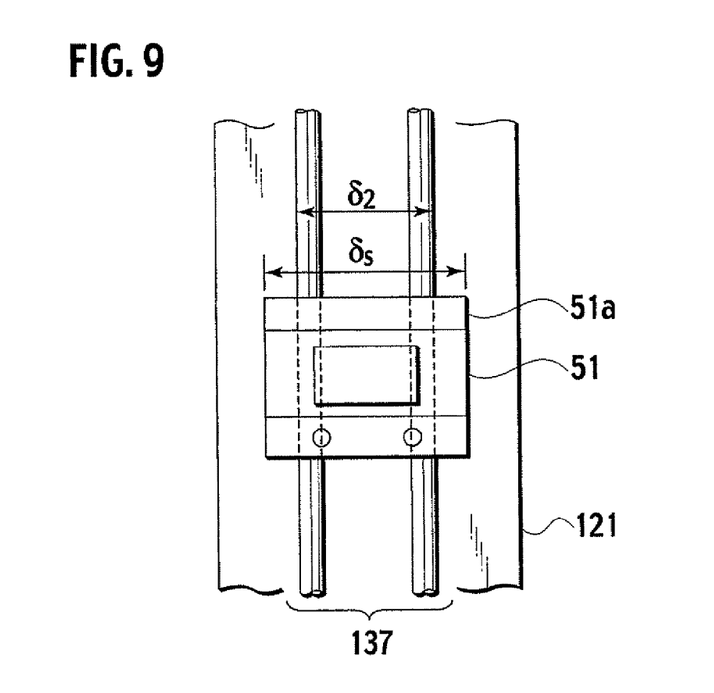
FIG. 9 is a view showing a state of the vibration suppressing mechanism with the second parallel linkage narrowed due to a tilt.

FIGS. 7 to 9 show the second parallel linkage P2 tilted and deformed according to a movement of the load L. With reference to FIG. 7, a tilt of the second parallel linkage P2 from a state A to a state B will be explained. Relative to the plate spring 51 fixed to the link case 121 (first longitudinal link k1), the first link shaft 137a moves away from the joint 19 in an xa-direction along the x-axis and the second link shaft 137b moves toward the joint 19 in an xb-direction along the x-axis. In connection with the y-axis direction, the first and second link shafts 137a and 137b move away from each other to a width δ1 as shown in FIG. 8, and then, move toward each other to a width δ2 into the state B as shown in FIG. 9. A tilt of the second parallel linkage P2 from the state B to the state A shown in FIG. 7 will be explained. Relative to the plate spring 51 fixed to the link case 121, the first link shaft 137a moves toward the joint 19 in an xc-direction along the x-axis and the second link shaft 137b moves away from the joint 19 in an xd-direction along the x-axis. In connection with the y-axis direction, the first and second link shafts 137a and 137b move away from each other as shown in FIG. 8, and then, move toward each other into the sate A as shown in FIG. 9.

In this way, when the second parallel linkage P2 tilts, the position of the link shaft 137 relative to the plate spring 51 fixed to the link case 121 changes in the x-axis and y-axis directions. According to the embodiment, the distal end 51a of the plate spring 51 has the surface pn that is parallel to the virtual plane (x-y) in which the link shaft 137 that defines a tilt of the second parallel linkage P2 moves. Accordingly, the distal end 51a and the link shaft 137 are always in contact with each other even if the second parallel linkage P2 tilts and deforms, and the distal end 51a slides along the side face 138 of the rigid link shaft 137. The interaction between the distal end 51a of the plate spring 51 and the side face 138 of the link shaft 137 is maintained even if the width δ of the second parallel linkage P2 changes, to surely suppress small vibrations of the second parallel linkage P2.

According to the embodiment, the link shaft 137 consists of the two link shafts 137a and 137b made of rigid material, and therefore, the link shaft 137 is rigid and causes no meaningful deformation with respect to a tensile or compressive force applied thereto. The two parallel sub-linkages (P2A, P2B) that form the second parallel linkage P2 always work so that the effective width of the second parallel linkage P2 will be substantially a physical width thereof δ to efficiently suppress small vibrations. According to an embodiment of the present invention, the link shaft 137 may be a single rigid shaft reducing the width of the second parallel linkage P2.

Employing the rigid link shaft 137 as a link of the second parallel linkage P2 results in reducing the width δ of the linkage P2 while securing a force transmission ability that is essential for maintaining the orientation of the front link 27 to a vertical direction. Narrowing the width δ of the linkage P2 results in reducing a working radius, thereby increasing the force transmission ability. This, however, may tend to produce small vibrations. Such small vibrations can surely be suppressed by the vibration suppressing mechanism 50. The vibration suppressing mechanism 50 is significantly effective when the medical stand with the vibration suppressing mechanism 50 is used to support a high-power microscope.

The link shaft 137 and plate spring 51 are housed in the hollow structure of the link case 121, so that no dust will enter the hollow structure in which the plate spring 51 slides on the link shaft 137. The opening 60 of the link case 121 is for maintenance. To cover the opening 60 and vibration suppressing mechanism 50 during the use of the medical stand, a cover 123 is removably attached to the body 122 of the link case 121. To prevent the plate spring 51 from vibrating, a damper 52 made of, for example, rubber may be attached to the plate spring 51 as shown in FIGS. 5 and 6.

The torque transmitting mechanism for a medical stand according to the present invention includes the second quadrilateral linkage having the third longitudinal link that is made of rigid material, as well as the vibration suppressing mechanism to suppress small vibrations without preventing a tilting operation of the second quadrilateral linkage. As a result, the second quadrilateral linkage can have a reduced width without causing small vibrations in the torque transmitting mechanism. The torque transmitting mechanism, therefore, can be used for a medical tool that is sensitive to small vibrations.

In the embodiment mentioned above, the medical tool supported with the medical stand is a surgical microscope. The medical stand of the present invention is applicable to support not only optical medical tools but also any other medical equipment that is sensitive to small vibrations.

In summary, the medical stand according to the present invention has the weight balancing mechanism, the torque transmitting mechanism for maintaining an attitude of a medial tool supported with the medical stand, and the vibration suppressing mechanism provided for the torque transmitting mechanism. The vibration suppressing mechanism can always suppress small vibrations of the torque transmitting mechanism even if the width of a parallel linkage included in the torque transmitting mechanism is narrowed. The medical stand allows an operator to stably observe an affected part to be operated with a high-power microscope that is supported with the medical stand and is vulnerable to small vibrations.

This application claims benefit of priority under 35USC §119 to Japanese Patent Applications No. 2006-274182, filed on Oct. 5, 2006, the entire contents of which are incorporated by reference herein. Although the invention has been described above by reference to certain embodiments of the invention, the invention is not limited to the embodiments described above. Modifications and variations of the embodiments described above will occur to those skilled in the art, in light of the teachings. The scope of the invention is defined with reference to the following claims.

What is claimed is:

1. A medical stand including:
a first parallel linkage (P1) linked through a first articulation (β1), a second articulation (β2), a third articulation (β3) opposing the first articulation, and a fourth articulation (β4) opposing the second articulation, the first and fourth articulations being linked to each other with a first longitudinal link (121), the second and third articulations being linked to each other with a second longitudinal link (22) extending in parallel with the first longitudinal link (121), the first and second articulations being linked to each other with a first lateral link (23), the third and fourth articulations being linked to each other with a second lateral link (24) extending in parallel with the first lateral link,
a fifth articulation (19) positioned at the first longitudinal link (121) between the first articulation (β1) and the fourth articulation (β4) and adapted to be fixed to a stand body (18) of the medical stand, an eighth articulation (β5) fixed relative to the first lateral link (23), and the third articulation (β3) supporting a counter weight (W1, W2);
a torque transmitting mechanism comprising:
a second parallel linkage (P2) linked through the first articulation (β1), the fifth articulation (19), a sixth articulation (β18) opposing the first articulation and fixed to the stand body, and a seventh articulation (β16) opposing the fifth articulation, the sixth and seventh articulations being linked to each other with a third longitudinal link (137) extending in parallel with the first longitudinal link (121), the first and seventh articulations being linked to each other with a third lateral link (β1-β16), the fifth and sixth articulations being linked to each other with a fourth lateral link (β18-19) extending in parallel with the third lateral link; and
a third parallel linkage (P3) linked through the first articulation (β1), the eighth articulation (β5), a ninth articulation (β9) opposing the first articulation, and a tenth articulation (β7) opposing the eighth articulation, the first and eighth articulations being linked to each other with a fifth lateral link (26), the ninth and tenth articulations being linked to each other with a sixth lateral (38) link extending in parallel with the fifth lateral link (26), the first and tenth articulations being linked to each other with a fifth longitudinal link (β1-β7), the eighth and ninth articulations being linked to each other with a sixth longitudinal link (27) extending in parallel with the fifth longitudinal link, the third lateral link (β1-β16) and fifth longitudinal link (β1)-(β7) being connected with a connecting element (34), the sixth longitudinal link (27) being always in parallel with plumb direction (g), the eighth articulation (β5) supporting a medical tool (L) just below the same, wherein:
the first and third longitudinal links are made of rigid material;
the third longitudinal link (137) is a link shaft; and
a vibration suppressing mechanism (50) is fixed relative to the first longitudinal link (121) and configured to always bias a side face (138) of the third longitudinal link (137) and produce contact resistance and slide resistance against relative movement thereof to suppress vibration of the third longitudinal link (137) that defines a tilt of the second parallel linkage (P2),
wherein the vibration suppressing mechanism comprises a plate spring having a proximal end fixed to the first longitudinal link and a distal end being always resiliently in contact with a side face of the third longitudinal link.

2. The medical stand according to claim 1, wherein the first longitudinal link is a link case having a hollow structure that houses the second parallel linkage and vibration suppressing mechanism.

3. The medical stand according to claim 1, wherein the third longitudinal link comprises two parallel longitudinal link elements.

4. The medical stand according to claim 1, wherein the distal end of the plate spring has a surface that is in linear or planar contact with a virtual plane defined by a movement of the third longitudinal link due to a tilt of the second quadrilateral linkage.

5. The medical stand according to claim 1, wherein:
the fifth articulation includes a rotary shaft that defines a tilt of the second parallel linkage; and
the distal end of the plate spring has a surface that is orthogonal to the rotary shaft and is always in linear or planar contact with a side face of the third longitudinal link.

6. The medical stand according to claim 1, wherein
the vibration suppressing mechanism has a damper at a proximal portion of the plate spring.

7. The medical stand according to claim 3, wherein
the two longitudinal link elements are equally spaced with respect to the first longitudinal link.

8. The medical stand according to claim 2, wherein the link case includes:
an opening formed at a position where the vibration suppressing mechanism and the third longitudinal link interact with each other; and
a detachable cover configured to cover the opening.

9. The medical stand according to claim 1, wherein the medical tool is a surgical microscope.

* * * * *